(12) United States Patent
Levitsky et al.

(10) Patent No.: US 9,636,043 B2
(45) Date of Patent: May 2, 2017

(54) EXHALED BREATH SAMPLING WITH DELIVERY OF GAS

(71) Applicant: Oridion Medical 1987 Ltd., Jerusalem (IL)

(72) Inventors: Gershon Levitsky, Jerusalem (IL); David Lain, Easton, MD (US); Joshua Lewis Colman, Jerusalem (IL)

(73) Assignee: Oridion Medical 1987 Ltd., Jerusalem (IL)

( * ) Notice: Subject to any disclaimer, the term of this patent is extended or adjusted under 35 U.S.C. 154(b) by 168 days.

(21) Appl. No.: 14/706,050

(22) Filed: May 7, 2015

(65) Prior Publication Data

US 2015/0230731 A1     Aug. 20, 2015

Related U.S. Application Data

(63) Continuation of application No. 12/651,594, filed on Jan. 4, 2010, now Pat. No. 9,055,888.

(60) Provisional application No. 61/193,889, filed on Jan. 5, 2009.

(51) Int. Cl.

| | |
|---|---|
| *A61B 5/08* | (2006.01) |
| *A61B 5/097* | (2006.01) |
| *A61B 5/083* | (2006.01) |
| *A61M 16/00* | (2006.01) |
| *A61M 16/06* | (2006.01) |
| *A61M 16/08* | (2006.01) |
| *A61M 16/10* | (2006.01) |

(52) U.S. Cl.
CPC .......... *A61B 5/097* (2013.01); *A61B 5/0836* (2013.01); *A61M 16/0003* (2014.02); *A61M 16/0057* (2013.01); *A61M 16/0666* (2013.01); *A61M 16/085* (2014.02); *A61M 16/1005* (2014.02); *A61M 2016/003* (2013.01); *A61M 2205/3334* (2013.01); *A61M 2230/42* (2013.01); *A61M 2230/432* (2013.01)

(58) Field of Classification Search
USPC .................................................. 600/532, 543
See application file for complete search history.

(56) References Cited

U.S. PATENT DOCUMENTS

| | | |
|---|---|---|
| 5,626,131 A | 5/1997 | Chua |
| 6,186,958 B1 | 2/2001 | Katzman |
| 6,422,240 B1 | 7/2002 | Levitsky |
| | (Continued) | |

FOREIGN PATENT DOCUMENTS

| | | |
|---|---|---|
| EP | 1849491 | 10/2007 |

*Primary Examiner* — Michael Kahelin
*Assistant Examiner* — Mitchell E Alter
(74) *Attorney, Agent, or Firm* — Fletcher Yoder PC

(57) ABSTRACT

A system for sampling exhaled breath and for supply of a gas, the system comprising: a gas delivery cannula comprising at least one nasal prong for insertion into a nostril, the nasal prong comprising a distal end; an exhaled breath sampling cannula for insertion into the nostril, the exhaled breath sampling cannula comprising a distal end; and a connector for coupling the gas delivery cannula to the exhaled breath sampling cannula, such that the distal end of the exhaled breath sampling cannula is disposed deeper in the nostril than the distal end of the nasal prong, to reduce dilution of sampled exhaled breath by delivered gas. The connected is configured to facilitate adjustability of an insertion depth of the exhaled breath sampling cannula into said nostril.

11 Claims, 8 Drawing Sheets

(56) References Cited

U.S. PATENT DOCUMENTS

| | | |
|---|---|---|
| 2001/0031929 A1 | 10/2001 | O'Toole |
| 2002/0017300 A1 | 2/2002 | Hickle |
| 2003/0127094 A1* | 7/2003 | Roberts ............ A61M 16/0666 128/203.22 |
| 2006/0155206 A1 | 7/2006 | Lynn |
| 2007/0095347 A1 | 5/2007 | Lampotang |
| 2009/0050154 A1 | 2/2009 | Strothmann |
| 2009/0165795 A1 | 7/2009 | Nadjafizadeh |

* cited by examiner

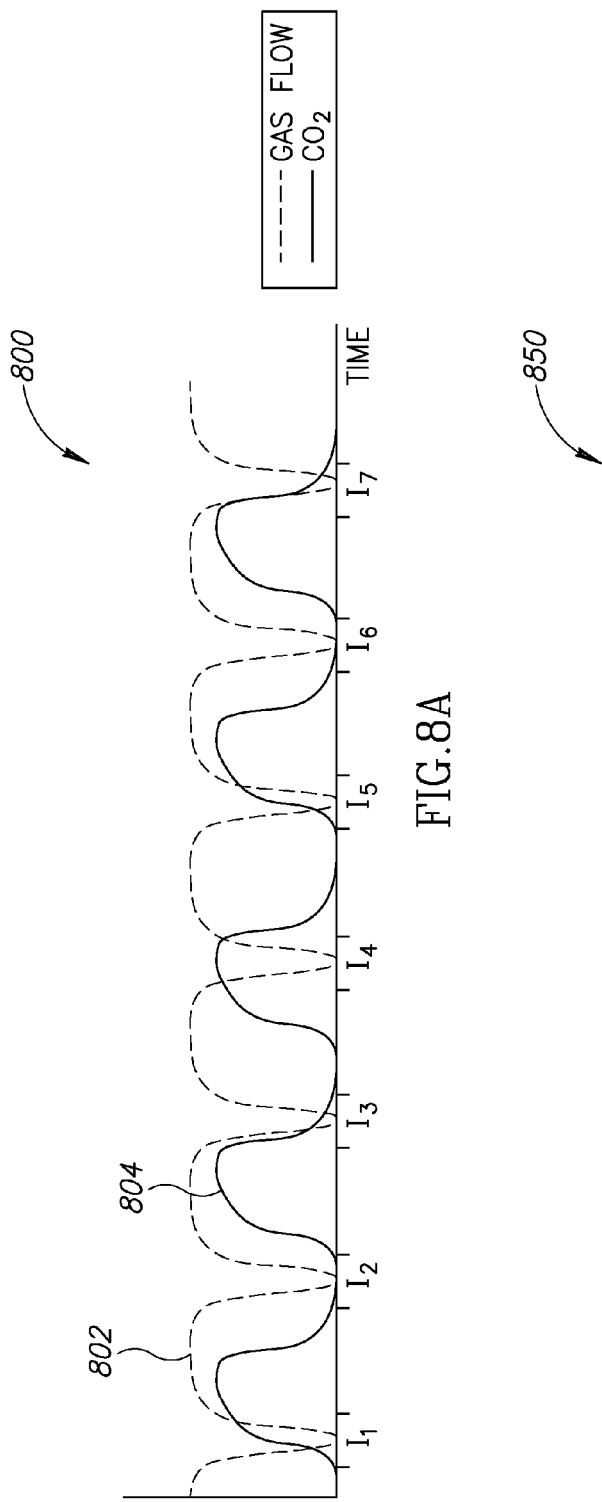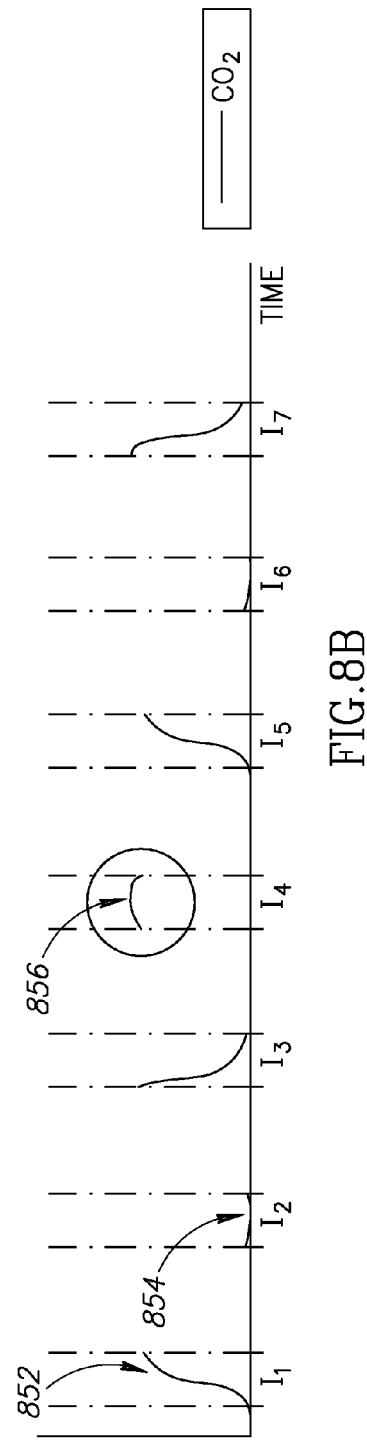
FIG.8A
FIG.8B

EXHALED BREATH SAMPLING WITH DELIVERY OF GAS

CROSS REFERENCE TO RELATED APPLICATIONS

This application claims the benefit of U.S. Provisional Patent Application No. 61/193,889, filed Jan. 5, 2009 and entitled "Exhaled Breath Sampling with Delivery of Gas", which is incorporated herein by reference in its entirety.

FIELD

Embodiments of the disclosure relate to exhaled breath sampling with delivery of gas.

BACKGROUND

For some breathing disorders, the treatment may include delivery of a medicinal gas, sometimes at a relatively high flow rate. The provided gas is sometimes oxygen. Mask and tent oxygen therapy has been available for a long time. Conventional oxygen masks and appliances usually comprise tent-like structures that are usually strapped over the nose and mouth of a patient to create a fluidic pathway for gaseous medicaments or other gases.

Another current approach to gas delivery to a patient employs a small bore flexible tube with tubular open-ended nasal prongs and/or holes (jointly referred to as a cannula). Cannulae may be preferred over masks at times because it is often believed that cannulae are more comfortable than masks, they create a greater oxygen reservoir in the posterior pharynx and/or sinuses, and they create a better laminar flow and positive flow when respiratory effort is low.

Medicinal gasses delivered through oral and/or nasal cannulae have traditionally been limited, at least according to the literature, to a maximum of approximately 8 liters per minute (L/m). This was usually the result of the physical limitations of design, such as the physics of greater flow though a relatively small bore. Other limitations have included mucosal drying, gas delivery outside of a target area, delivery outside of target BTPS (Body Temperature and Pressure Saturated) values, discomfort and/or the like.

A high flow, warmed and humidified nasal oxygen delivery system that comfortably delivers nasal oxygen up to 40 L/m was recently introduced by Vapotherm, Inc., of Stevensville, Md.

While the medicinal gas is being delivered, it is often desired to obtain measurements of exhaled breath, in order to evaluate the patient's condition—whether his respiratory condition or a different medical condition.

An example of one of the many possible measurements of exhaled breath is Capnography, often defined as the measurement of the level of carbon dioxide ($CO_2$). Since infrared light was found to be absorbed particularly well by $CO_2$, capnographs usually measure infrared absorption in the breath gasses, which indicates the level of $CO_2$ in these gasses. Other measurement technologies exist as well. The information obtained from a capnographic measurement is sometimes presented as a series of waveforms, representing the partial pressure of $CO_2$ in the patient's exhaled breath as a function of time. Clinicians commonly use capnography in order to assess a patient's ventilatory status. Respiratory arrest and shunt may be speedily diagnosed, and a whole range of other respiratory problems and conditions may be determined by the capnographic measurement. Capnography is considered to be a prerequisite for safe intubation and general anesthesia, and for correct ventilation management.

SUMMARY

There is provided, according to an embodiment, a system for sampling exhaled breath and for supply of a gas, the system comprising a gas delivery cannula comprising at least one nasal prong for insertion into a nostril, said nasal prong comprising a distal end; an exhaled breath sampling cannula for insertion into said nostril, said exhaled breath sampling cannula comprising a distal end; and a connector for coupling said gas delivery cannula to said exhaled breath sampling cannula, such that the distal end of said exhaled breath sampling cannula is disposed deeper in said nostril than the distal end of said nasal prong, to reduce dilution of sampled exhaled breath by delivered gas, wherein said connected is configured to facilitate adjustability of an insertion depth of said exhaled breath sampling cannula into said nostril.

In some embodiments, said exhaled breath sampling cannula further comprises multiple scale marks indicating gas flow rates, so that said adjustability of the insertion depth can be correlated with a flow rate of delivered gas.

In some embodiments, said exhaled breath sampling cannula further comprises multiple apertures adjacent to the distal end of said exhaled breath sampling cannula.

In some embodiments, said nasal prong of said gas delivery cannula further comprises multiple apertures adjacent to the distal end of said nasal prong.

In some embodiments, the system further comprises a capnograph connected to a proximal end of said exhaled breath sampling cannula, for measuring a carbon dioxide ($CO_2$) level in exhaled breath.

In some embodiments, the system further comprises a gas flow generator connected to said gas delivery cannula, for delivering gas through said gas delivery cannula.

In some embodiments, said gas comprises oxygen.

In some embodiments, said exhaled breath sampling cannula is adapted to sample the exhaled breath for measuring a $CO_2$ level.

There is further provided, according to an embodiment, an apparatus for sampling exhaled breath and for supply of a gas, the apparatus comprising a gas delivery cannula comprising at least one nasal prong, said nasal prong comprising a distal end; and an exhaled breath sampling cannula comprising a distal end, wherein said nasal prong and said exhaled breath sampling cannula are attached together along a portion of their length, such that the distal end of said exhaled breath sampling cannula protrudes beyond the distal end of said nasal prong, to reduce dilution of sampled exhaled breath by delivered gas.

There is further provided, according to an embodiment, a cannula for sampling exhaled breath and for supply of a gas, the cannula comprising a gas delivery channel extending internally inside the cannula and terminating at a distal end; and an exhaled breath sampling channel extending internally inside the cannula and terminating at a distal end positioned beyond the distal end of said gas delivery channel, to reduce dilution of sampled exhaled breath by delivered gas.

There is further provided, according to an embodiment, a system for sampling exhaled breath and for supply of a gas, the system comprising an exhaled breath sampling cannula for insertion into a first nostril of a patient; and a gas delivery cannula comprising at least one nasal prong adapted for insertion into a second nostril of the patient, said nasal prong having a plurality of apertures for dispersing delivered gas so as to reduce dilution of sampled exhaled breath by delivered gas in a nasal cavity of the patient.

There is further provided, according to an embodiment, a system for sampling of exhaled breath and for supply of a gas, the system comprising a gas delivery cannula comprising at least one nasal prong for insertion into a nostril, said nasal prong comprising multiple outlet apertures for dispersing delivered gas so as to reduce dilution of sampled exhaled breath by delivered gas; and an exhaled breath sampling cannula for insertion into said nostril, said exhaled breath sampling cannula comprising a distal end configured to be disposed at approximately the same depth in the nostril as the outlet apertures of said nasal prong.

In some embodiments, the system further comprises a capnograph connected to said exhaled breath sampling cannula, for measuring a $CO_2$ level.

In some embodiments, the system further comprises a gas flow generator connected to said gas delivery cannula, for delivering gas.

In some embodiments, said gas comprises oxygen.

There is further provided, according to an embodiment, a method for measuring exhaled breath of a patient being supplied with a gas, the method comprising providing the patient with a flow of a gas; reducing the flow of the gas for a predetermined period; sampling an exhaled breath of the patient while the flow of the gas is reduced, to reduce dilution of the exhaled breath by the flow of the gas.

In some embodiments, the reducing of the flow of the gas comprises stopping the flow of the gas.

In some embodiments, the sampling of the exhaled breath comprises: performing a first sampling during a first exhalation of the patient, wherein previously provided gas is substantially discarded by the patient during the first exhalation; and performing a second sampling during a second exhalation of the patient, wherein a concentration of previously provided gas in the second exhalation is lower than a concentration of previously provided gas in the first exhalation.

In some embodiments, the method further comprises calculating a respiration rate of the patient, based on a measured interval between the first sampling and the second sampling; and adjusting the predetermined period based on the respiration rate, so that the predetermined period extends over essentially two consecutive exhaled breaths.

In some embodiments, the method further comprises identifying an exhalation timing using a flow sensor; and synchronizing the predetermined period to extend over essentially two identified exhaled breaths.

In some embodiments, the method further comprises estimating an end-tidal $CO_2$ ($EtCO_2$) level based on a highest $CO_2$ peak detected in at least one of a plurality of samplings.

There is further provided, according to an embodiment, a system for sampling exhaled breath and for supply of a gas, the system comprising a nose continuer for nasally providing gas to a patient, and comprising a gas inlet for connection to a gas source; and an exhaled breath sampling cannula for insertion into a nostril, said exhaled breath sampling cannula comprising a distal end, wherein a distance between said distal end and the gas inlet of said nose continuer is such that dilution of sampled exhaled breath by provided gas is reduced.

There is further provided, according to an embodiment, a system for sampling exhaled breath and for supply of a gas, the system comprising an oral-nasal mask for providing gas to a patient, said mask comprising a gas inlet for connection to a gas source; and an exhaled breath sampling cannula for insertion into a nostril, said exhaled breath sampling cannula comprising a distal end, wherein a distance between said distal end and the gas inlet of said oral-nasal mask is such that dilution of sampled exhaled breath by provided gas is reduced.

There is further provided, according to an embodiment, a system for sampling exhaled breath and for supply of a gas, the system comprising a gas delivery cannula; a flow sensor configured to identify a timing and an intensity of an exhaled breath; an exhaled breath sampling cannula; and a controller configured to synchronize sampling of exhaled breath with said timing and intensity, such that exhaled breath is sampled when at a peak of said intensity.

In some embodiments, said controller is further configured to reduce gas delivery at essentially said peak of intensity.

There is further provided, according to an embodiment, a system for sampling exhaled breath and for supply of a gas, the system comprising an exhaled breath sampling cannula comprising a nasal prong; and an aerodynamic gas regulator comprising a diffuser and a nasal prong, said regulator being configured to supply gas through both of said diffuser and said nasal prong during inhalation, and to supply gas primarily through said diffuser during exhalation, so that dilution of sampled exhaled breath by supplied gas is reduced during exhalation.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. It is intended that the embodiments and figures disclosed herein are to be considered illustrative rather than restrictive. The figures are listed below.

FIGS. 8A-8B, show graphs of methods for measuring exhaled breath of a patient being supplied with a gas;

DETAILED DESCRIPTION

Figure 1:
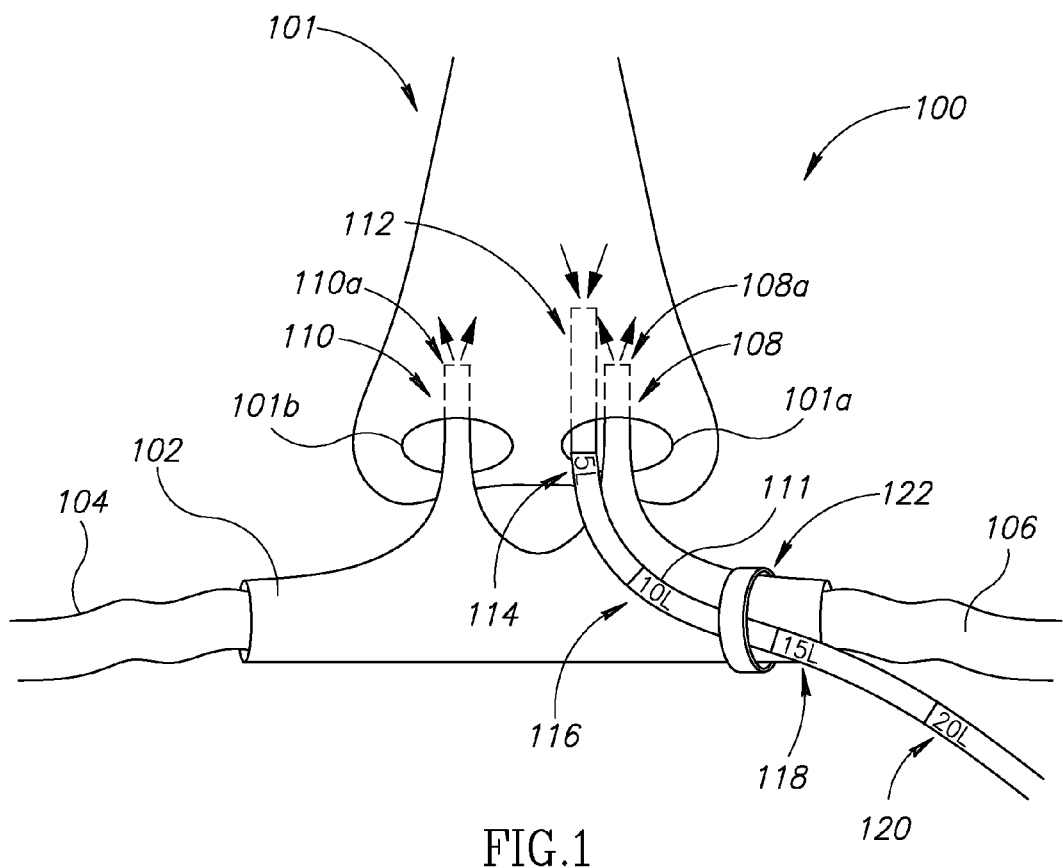
FIGS. 1-5 show systems adapted for sampling exhaled breath and for supply of a gas.

An aspect of some embodiments relates to systems, apparatuses and methods for sampling exhaled breath of a patient being provided with a medicinal gas. Medicinal gasses are often supplied to patients to treat respiratory and/or other medical problems. Sampling of exhaled breath of such patients and measuring concentration of one or more components in the sample may be beneficial in assessing the patient's medical condition via factors such as ventilation, perfusion, metabolism and/or the like.

However, the reliability of the sampling, if performed while the medicinal gas is being provided, may sometimes be questionable. The provided medicinal gas may dilute the patient's exhaled breath, thereby biasing the measurement of concentration in the sampled exhaled breath. That is, if an outlet of a medicinal gas supply cannula is positioned in the vicinity of an inlet of an exhaled breath sampling cannula, some of the supplied medicinal gas may penetrate into the sampling cannula and thus bias the measurement.

The dilution problem is sometimes aggravated as the flow rate of the supplied medicinal increases. In some scenarios, a medicinal gas is supplied at a relatively high flow rate, which may be expressed either by a relatively high volume of gas per minute being infused through a relatively large aperture, or by a relatively low volume of gas per minute being infused through a relatively small aperture. In both cases, a relatively high pressure of gas, also referred to as a high flow rate of the gas, is created at the aperture. If the inlet of the exhaled breath sampling cannula is positioned in the vicinity of this aperture, then naturally, more medicinal gas may enter the inlet as the flow rate of the medicinal gas increases.

High flow of gas supply is sometimes defined as approximately 2.5 Liters per minute (LPM) or more for neonates, 6 LPM or more for children, and 8 LPM or more for adults. However, other flow rates may also be referred to as "high", in different situations and for different patients.

The systems, apparatuses and methods disclosed herein, may enhance the reliability of the measurement of sampled exhaled breath by addressing one or more of the forms of the dilution problem discussed above.

The terms "medicinal gas", "supplied gas", "provided gas", "delivered gas" and any variation or permutation thereof, as referred to herein, may refer to any gas which may be provided to a patient for medical purposes. For example, the medicinal gas may be oxygen ($O_2$), oxygen-enriched air and/or the like (wherein oxygen-enriched air is also hereinafter referred to simply as "oxygen"). In some embodiments, the medicinal gas may be humidified and/or warmed.

The terms "measurement", "concentration", "concentration measurement" and any variation or permutation thereof, as referred to herein in relation to sampling of exhaled breath, may refer to a measurement of concentration of one or more particular components, sometimes gaseous, in an exhaled breath. For example, a concentration of carbon dioxide ($CO_2$) and/or oxygen may be measured.

The term "sampling" and any variation thereof, as referred to herein, may refer to a suction force applied by a pump in order to draw gas (at times constituting a patient's exhaled breath), through a cannula, towards a device adapted to measure a concentration of one or more particular components, sometimes gaseous, in the drawn gas.

In a first sampling scenario, the sampling may be continuous, namely—gas may be sucked constantly towards the measurement device. In this scenario, the measurement device may or may not perform constant measurement on the sucked gas:

if constant measurement is performed, little or no weight may be given to measurements done when the flow of provided gas is relatively high, namely—to measurements suspected as biased. Additionally or alternatively, a higher weight may be given to measurements performed during a peak of exhalation, when there is usually a lesser chance of a bias. Yet another option, employed in some embodiments, is to give a high and low (or zero) weights according to a predetermined duty cycle.

if constant measurement is not performed, but the measurement device rather measures only at times when the flow of provided gas is low or zero, when an exhalation is at its peak and/or according to a predetermined duty cycle, then the measurement is not usually suspected as biased and may therefore be generally useful.

In a second sampling scenario, the sampling may be performed intermittently, namely—gas may be sucked towards the measurement device only when the flow of provided gas is low or zero, only when exhalation is at its peak, and/or according to a predetermined duty cycle. The intermittent suction of the gas may be synchronized with the measurement device, which may be configured to measure only when sampling it actually performed. Alternatively, the measurement device may perform constant measurements, but naturally only get a meaningful result when gas is actually sucked towards it.

It is hereby explicitly intended that the term "sampling", when used in conjunction with an embodiment of this disclosure, be interpreted, mutatis mutandis, to include all the relevant sampling scenarios and their sub-options which pertain to measurements, weight given to measurements and the like.

Reference is now made to FIG. 1, which shows a system 100 adapted for sampling exhaled breath and for supply of a gas. System 100 may include a gas delivery cannula 102 including at least one nasal prong adapted for insertion into a nose 101 of a patient. For example, gas delivery cannula 102 is shown having two nasal prongs 108 and 110 inserted into a first nostril 101*a* and into a second nostril 101*b*, respectively, of the patient's nose 101. Each of nasal prongs 108 and 110 may have a distal end 108*a* and 110*a*, respectively, through which gas may flow into nose 101. At least one of distal ends 108*a* and 110*a* may be rounded, to allow for greater comfort of the patient and/or to prevent injury to tissues as a result of rubbing against a coarse distal end.

At least one gas delivery tube, such as two tubes 104 and 106, may be connected to gas delivery cannula 102 from one side, and to a gas flow generator (not shown) from the other side. The gas flow generator may be adapted to provide gas delivery cannula 102 with a positive gas pressure.

System 100 may further include at least one exhaled breath sampling cannula, such as exhaled breath sampling cannula 111, which may be inserted into at least one of the nostrils in which a nasal prong 108 and/or 110 is inserted, such as into nostril 101*a*. Exhaled breath sampling cannula 111 may have a distal end 112, through which the patient's exhaled breath may enter the exhaled breath sampling cannula.

A concentration meter (not shown) may be connected to a proximal end (not shown) of exhaled breath sampling cannula 111, to measure concentration of one or more ingredients, optionally, gaseous, in exhaled breath sampled through the cannula. The concentration meter is optionally a capnograph (not shown), adapted to measure concentration of $CO_2$ in exhaled breath.

Distal end 112 of exhaled breath sampling cannula 111 may advantageously be disposed deeper in nostril 102*a* than distal end 108*a* of nasal prong 108, so that exhaled breath enters exhaled breath sampling cannula 111 at a location distant from where a positive gas pressure of the gas supply exists, namely—at distal end 108*a* of nasal prong 108. This may enhance the reliability of the concentration measurement, since dilution of exhaled breath by provided gas is substantially reduced compared to a configuration where distal ends of a gas supply nasal prong and exhaled breath sampling cannula are substantially adjacent.

System 100 may further include at least one connector, such as a ring 122, adapted to couple and secure exhaled breath sampling cannula 111 and gas delivery cannula 102 together. Coupling exhaled breath sampling cannula 111 and gas delivery cannula 102 may help ensure that a desired insertion depth of distal end 112 in relation to distal end 108a is kept. Additionally, ring 122 may facilitate adjustability of the insertion depth of exhaled breath sampling cannula 111, by forming a sort of a track for relative movement of the exhaled breath sampling cannula and gas delivery cannula 102. This may assist a caregiver in accurately adjusting the insertion depth. Persons of skill in the art will recognize that a wide range of physical elements may serve as a connector. For example, even a piece of adhesive tape may be used to hold exhaled breath sampling cannula 111 and gas delivery cannula 102 together, although an adhesive tape may not allow for the adjustability mentioned.

Optionally, exhaled breath sampling cannula 111 may include multiple scale marks, such as scale marks 114-120, indicating gas flow rates. For example, scale marks 114-120 are shown bearing indications of 5 liters of gas flow per minute, 10 liters, 15 liters and 20 liters, respectively. Similarly, other scale marks (not shown) may indicate gas flow rates at different intervals, different measurement units and/or the like. Scale marks 114-120 may be printed on a surface of exhaled breath sampling cannula 111, engraved upon the surface and/or the like.

Scale marks 114-120 may be used by a caregiver, while adjusting an insertion depth of exhaled breath sampling cannula 111, to correlate the depth with a flow rate of gas supplied through gas delivery cannula 102. Since a greater gas flow rate may cause greater dilution of sampled exhaled breath, distal end 112 of exhaled breath sampling cannula 111 should be inserted deeper into nostril 112 and farther away from distal end 108a as the gas flow rate increases, so that dilution is minimized. Usage of scale marks 114-120 may be performed against a reference point, such as the aperture of nostril 101a or a reference point indicated on gas delivery cannula 102.

Figure 2:
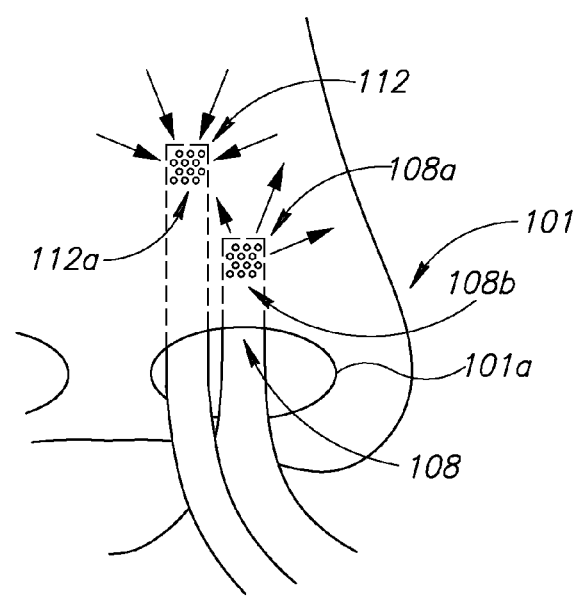

Reference is now made to FIG. 2, which shows an optional variation of system 100 of FIG. 1. At least one of nasal prong 108 and exhaled breath sampling cannula 111 may include multiple apertures adjacent to its distal end. For example, nasal prong 108 may have multiple apertures 108b near its distal end 108a, aimed at dispersing the gas supplied through the nasal prong so that not all of it exits at the distal end. Distal end 108a may even be closed, so that the gas exists only at apertures 108a. Optionally, in addition to or instead of apertures 108b, nasal prong 108 may include an area, at least next to its distal end 108a, made of a porous material allowing provided gas to diffuse through its pores, thereby dispersing spatially into the nose. Dispersion of the supplied gas may enhance reliability of measurement of exhaled breath, since the gas is dispersed and does essentially cause high pressure at a single point next to distal end 108a. Further, during exhalation, the exhaled air may more easily push back the dispersed gas from reaching to the deeper-in distal end of exhaled breath sampling cannula 111. Optionally, if apertures 108b exist, exhaled breath sampling cannula 111 may be positioned at a same height (not shown) with nasal prong 108, although the exhaled breath sampling cannula may still be inserted deeper.

As another example, exhaled breath sampling cannula 111 may include multiple apertures 112b adjacent to its distal end 112, and the distal end may be open or closed. In this case, apertures 112b may enable sampling even when distal end 112 is obstructed, such as when it is pushed, on one of its sides or at its end, against the nose's internal tissue.

Figures 3, 4:
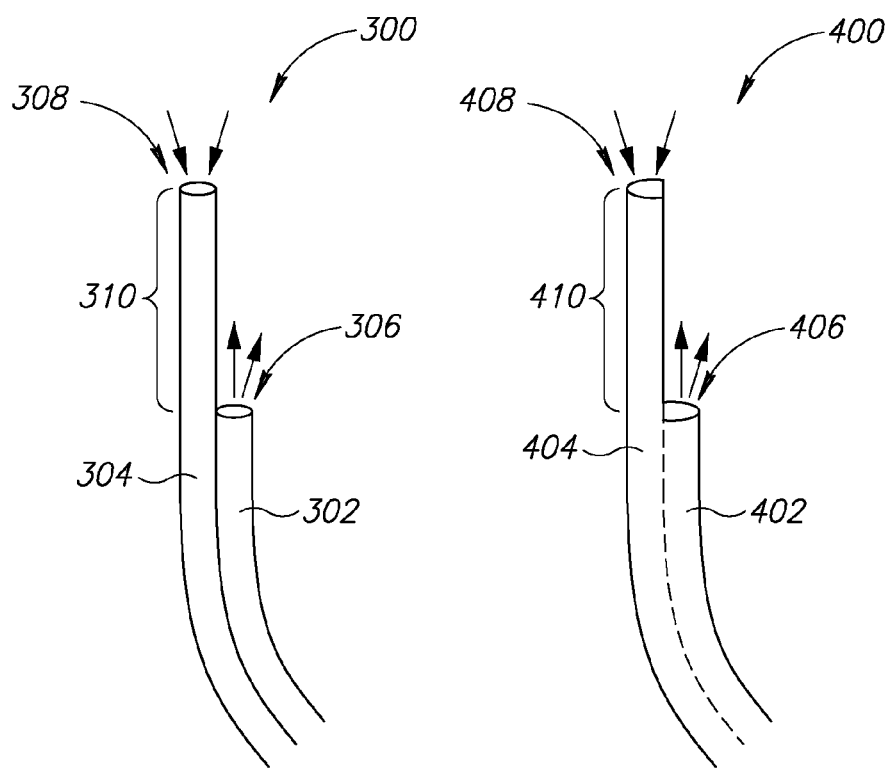

Reference is now made to FIG. 3, which shows another optional variation of system 100 of FIG. 1. An apparatus 300 for sampling exhaled breath and for supply of a gas is shown, the apparatus having a gas delivery cannula 302 and an exhaled breath sampling cannula 304 attached together. The attachment of gas delivery cannula 302 and exhaled breath sampling cannula 304 may be by virtue of a glue, fusion and/or the like. The attachment may be along a portion of the length of gas delivery cannula 302 and exhaled breath sampling cannula 304, such that a distal end 308 of exhaled breath sampling cannula 304 protrudes beyond a distal end 306 of gas delivery cannula 302. A protrusion length 310 may optionally be provided relatively long, so that a caregiver may adjust it to the pertinent gas flow rate by simply cutting it with scissors, a knife or the like.

Reference is now made to FIG. 4, which shows yet another optional variation of system 100 of FIG. 1. A single cannula 400 for sampling exhaled breath and for supply of a gas is shown, the cannula having at least two internal channels: a gas delivery channel 402 and an exhaled breath sampling channel 404. Similar to apparatus 300 of FIG. 3, exhaled breath sampling channel 405 may terminate at a distal end 408 positioned beyond a distal end 406 of gas delivery channel 402. Also similarly, a protrusion length 410 may optionally be provided relatively long, so that a caregiver may adjust it to the pertinent gas flow rate by simply cutting it with scissors, a knife or the like.

Figure 5:
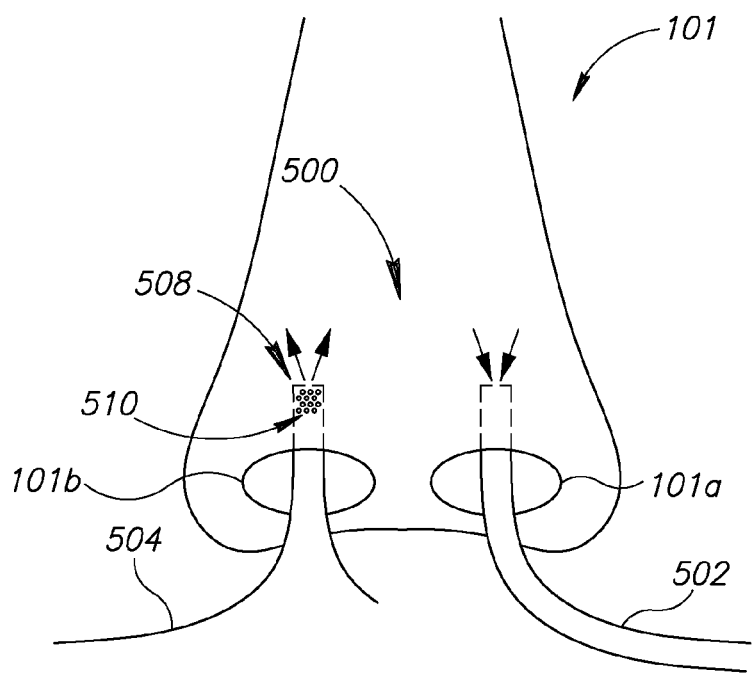

Reference is now made to FIG. 5, which shows another system 500 for sampling exhaled breath and for supply of a gas. System 500 may include a gas delivery cannula 504 having a nasal prong 508, and an exhaled breath sampling cannula 502, wherein the nasal prong and the exhaled breath sampling cannula are positioned in different nostrils. When positioning nasal prong 508 and exhaled breath sampling cannula 502 in different nostrils, dilution may still occur, since the supplied gas may flow, at a high pressure, into the nasal cavity where the two nostrils connect, and dilute the exhaled breath there. Therefore, nasal prong 508 may be provided with multiple apertures 510 for dispersing the gas supply, so that instead of high pressure, narrow angle injection of gas, the gas is provided at multiple angles, thereby decreasing dilution at the nasal cavity.

Figure 6:
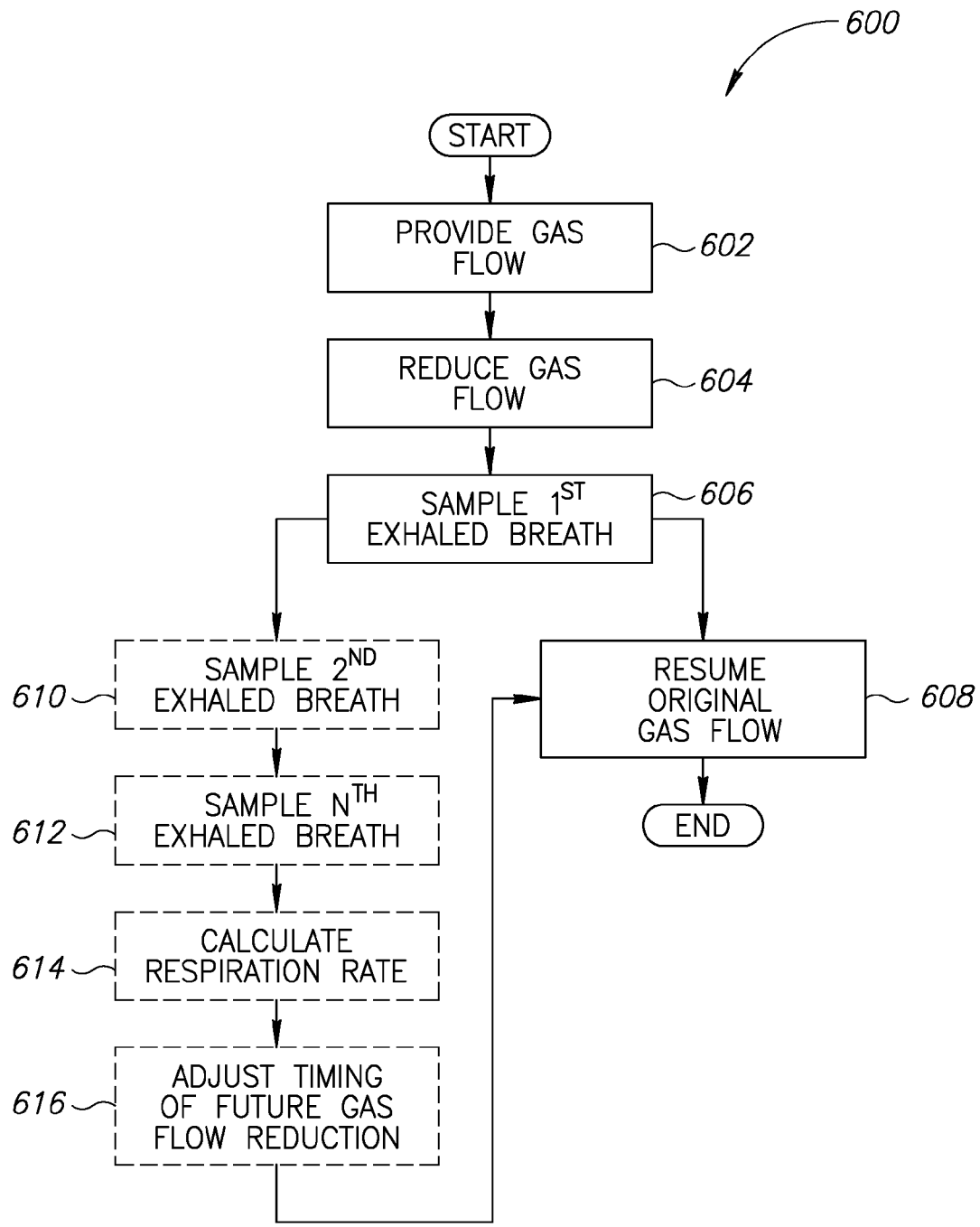
FIGS. 6-7 show flow charts of methods for measuring exhaled breath of a patient being supplied with a gas.

Reference is now made to FIG. 6, which shows a flow chart of a method 600 for measuring exhaled breath of a patient being supplied with a gas. Method 600 may be used in conjunction with any of the systems, apparatuses and cannulae of FIGS. 1-5, with a system of FIGS. 12A-12B, and/or with any other conventional system, such as, for example, a system which includes a simple gas delivery cannula and a simple exhaled breath sampling cannula, even disposed at a same nostril and at the same depth. Namely, method 600 may advantageously provide relatively good measurements of exhaled breath despite a physical configuration that would otherwise cause substantial dilution.

In a block 602, a flow of gas is provided to the patient through any means of gas delivery, such as a gas delivery cannula, a mask and/or the like.

In a block 604, the flow of gas is reduced. The term "reduced", as referred to herein, may also refer to a complete cessation of the flow.

In a block 606, sampling of exhaled breath, through any means of sampling, is performed. At least one exhaled breath may be sampled. When the flow of gas is at a reduced level, such as in block 606, the reliability of the measurements may be advantageously enhanced, since less of the supplied gas, or no supplied gas at all, enters the sampling means and dilutes the exhaled breath.

Following block 606, method 600 may split into two paths. In a first path, in a block 608, the flow of gas is resumed to its original level that existed in block 602, or to a different level higher than the reduced level of block 604. Method 600 may repeat itself from there.

In a second, optional path, extending over blocks 610-616, a more advanced way of sampling is used. In block 610, a second exhaled breath is sampled. Similarly, additional one or more consecutive exhaled breaths may be sampled in block 612. The sampling of additional one or more exhaled breaths may enable a calculation of a respiration rate of the patient, as described below in relation to a consequent block 614.

In block 614, a respiration rate of the patient may be calculated, based on the intervals between the exhaled breaths of blocks 606, 610 and optionally 612. For example, if two exhaled breaths were detected over a period of 6 seconds, then the respiration rate is 20 breaths per minute.

In a block 616, timing of future gas flow reductions (such as that of block 604) may be adjusted, based on the respiration rate calculated in block 614. Since we would generally like to reduce the gas flow for the shortest duration possible so that the patient's condition is not worsened, it may be advantageous to adjust the future flow reductions to last only over exactly one exhalation (if no further respiration rate calculations are desired) or two consecutive exhalations (for being able to calculate the respiration rate again, or for other purposes). When performing method 600 for the first time, the timing of the patient's respiration is not yet known, and therefore the flow of gas is reduced for an essentially arbitrarily predetermined period of time. However, past block 614, the respiration rate is already known, so future reductions of gas flow may be relatively accurately scheduled.

Additionally or alternatively, the timing of future gas flow reductions may be adjusted in a different way. If, for example, it is determined by the results of the measurement and/or by other medical factors, that sampling may be performed more rarely in the future—then a duration in which high flow is provided may be extended, and less measurements (and, therefore, less periods of low or zero flow) per time unit may be performed.

Following the adjustment of block 616, the original gas flow may be resumed, in block 608, and method 600 may be repeated.

Figure 7:
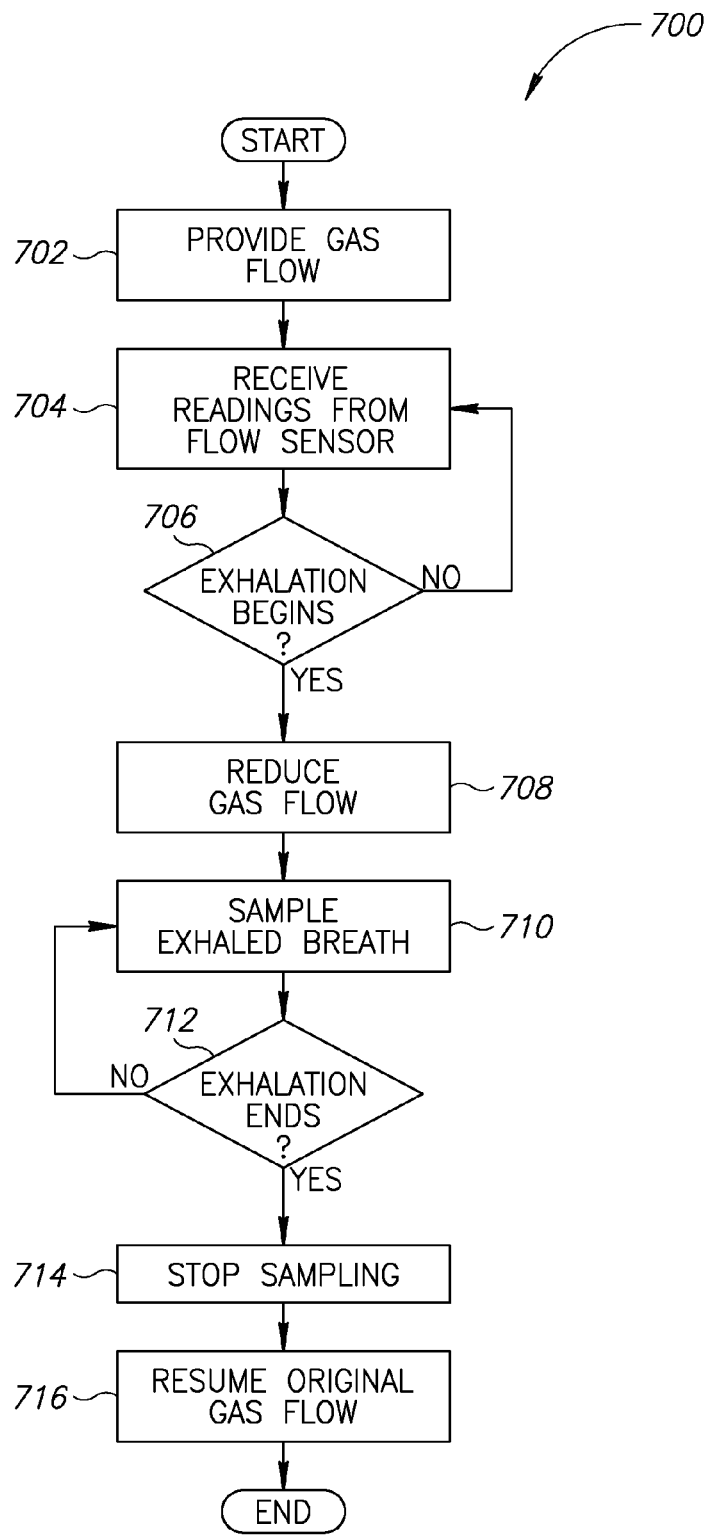

Reference is now made to FIG. 7, which shows a flow chart of another method 700 for measuring exhaled breath of a patient being supplied with a gas. In contrast to method 600 of FIG. 6, where the measurement device was used to calculate the respiration rate so that the predetermined period of sampling may be adjusted, method 700 utilizes a flow sensor which is adapted to identify the patient's exhalation timing. The flow sensor may be a pressure sensor positioned next to the patient's mouth or nose for detecting flow of air, a thermistor for detecting air temperature changes that are caused by the breathing, and/or the like. The usage of the flow sensor may allow detection of exactly when the patient exhales, so that the gas flow may be reduced for the minimal duration possible for covering the desired number of exhalations.

Advantageously, the use of the flow sensor may, additionally, enable a detection of one or more apnea events that occur when sampling is not performed, namely—when the flow is high. In contrast, apnea events occurring when the flow is low and sampling is performed, may be detected by the measurement device without the need of a flow sensor—as in method 600 of FIG. 6.

In a block 702, a flow of gas may be provided. In a block 704, readings may be received from the flow sensor, indicating a state of the respiration. In a decision block 706 it is determined, based on the readings from the flow sensor, if exhalation begins or is about to begin. It should be noted that the flow sensor may provide readings continuously, or provide only an indication that an exhalation begins or is about to begin. If the flow sensor continuously provides readings, an external controller may be used to perform the decision of decision block 706.

If it is determined that exhalation does not begin or is not about to begin, then more readings may be received from the flow sensor upon returning to block 704. If, however, it is determined that exhalation begins or is about to begin, then the gas flow may be reduced, in a block 708.

While the gas flow is reduced, one or more exhaled breaths may be sampled, in a block 710. As mentioned before, it may be desired to allow the patient exhale at least once to discard previously-supplied gas, before the measurements are treated as significant.

In a decision block 712, it is determined, based on readings from the flow sensor, if the first, second or $N^{th}$ exhalation (depending on the number of exhaled breaths samples/measured in block 710) ended. If it did not end, the sampling of block 710 may continue. If the exhalation did end, then the sampling may stop, in a block 714. Then, the original gas flow may be resumed, in a block 716, and method 700 may be repeated.

Reference is now made to FIGS. 8A and 8B, which show graphs 800 and 850, respectively, depicting an optional variation of method 600 of FIG. 6, in which an end-tidal $CO_2$ (EtCO$_2$) level may be estimated.

Graph 800 shows a providing of a gas flow at a predetermined duty cycle having essentially two levels of gas flow. The gas flow may be high for a certain duration and then low (or zero) for a consecutive duration. Exemplary gas flow curve 802 shows a gas flow supplied at an exemplary duty cycle of approximately 70%, wherein the flow is high for most of the time (70% of it) and essentially zero for a smaller fraction of the time (30%). Since when stopping the gas flow supply the actual pressure does not usually stop at once, gas flow curve 802 is shown as a sinusoidal wave and not as a square wave. The durations in which the gas flow is reduced are marked $I_1, I_2, \ldots, I_7$.

Simultaneously, $CO_2$ levels may be measured in the patient's exhaled breath. $CO_2$ curve 804 shows a theoretical, common waveform of $CO_2$ in exhaled breath that may be produced in the measurement, should the measurement be continuous. However, since the gas flow may dilute the exhaled breath and distort the $CO_2$ measurement, significance is only given to those parts of the measurement that were made during the reduced flow periods, namely—$I_1, I_2, \ldots, I_7$. Alternatively, sampling/measurement may only be performed during these reduced flow periods.

Graph 850 shows the portions of $CO_2$ curve 804 that fall within periods $I_1, I_2, \ldots, I_7$. For example, in period $I_1$, $CO_2$ curve 804 saw a steep increase 852; in period $I_2$, $CO_2$ curve 804 demonstrated an almost zero state 854, whereas in period $I_4$, $CO_2$ curve 804 demonstrated a peak 856 in the $CO_2$ level.

Peak 856, by definition, constitutes an EtCO$_2$ point, and therefore its numeral value may be relayed to a caregiver interested in knowing the current EtCO$_2$ level of the patient. It should be noted that since the chosen duty cycle is most likely not synchronized with the patient's $EtCO_2$ points (except if such synchronization happened accidentally), multiple breathing cycles may pass until a peak that falls within the reduced flow periods is discovered. However, even a $EtCO_2$ level that is indicated once every few minutes (or even more) may be advantageous.

Optionally, a flow sensor may be used to dynamically adjust the duty cycle so that periods of reduced flow are approximately synchronized with the patient's subjective $EtCO_2$ points. That is, the flow sensor may detect the timing and intensity of exhalation, thereby informing of the best time to capture the $EtCO_2$ points.

Figure 9:
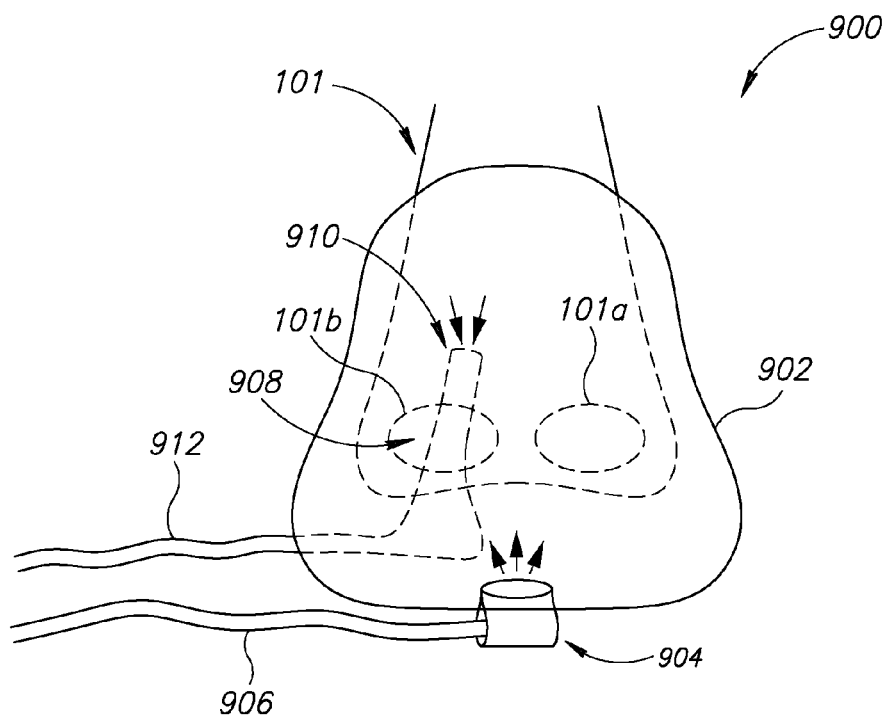
FIGS. 9-10 show systems adapted for sampling exhaled breath and for supply of a gas.

Reference is now made to FIG. 9, which shows a system 900 adapted for sampling exhaled breath and for supply of a gas. System 900 may include a nose continuer 902 adapted to provide gas supply to a patient through the nose. Nose continuer 902 may be any device, cover, mask and/or the like that provides a space covering nose 101 at least from slightly above nostrils 101a-b and down to an area between nose 101 and the mouth (not shown).

Nose continuer 902 may include a gas inlet 904 connecting it to a gas source through a gas cannula 906. Gas inlet 904 may be positioned at any location of nose continuer 902 which is relatively distant from nostrils 101a-b. In FIG. 9, gas inlet 904 is shown, as an example, at a lower part of nose continuer 902.

System 900 may further include an exhaled breath sampling cannula 912 having one or two nasal prongs; for example, it may have a single nasal prong 908 including a distal end 910.

When gas is supplied through gas inlet 904 and exhaled breath is sampled through distal end 910, the enlarged distance between the two may reduce dilution of exhaled breath by supplied gas, thereby improving the reliability of the measurement.

Figure 10:
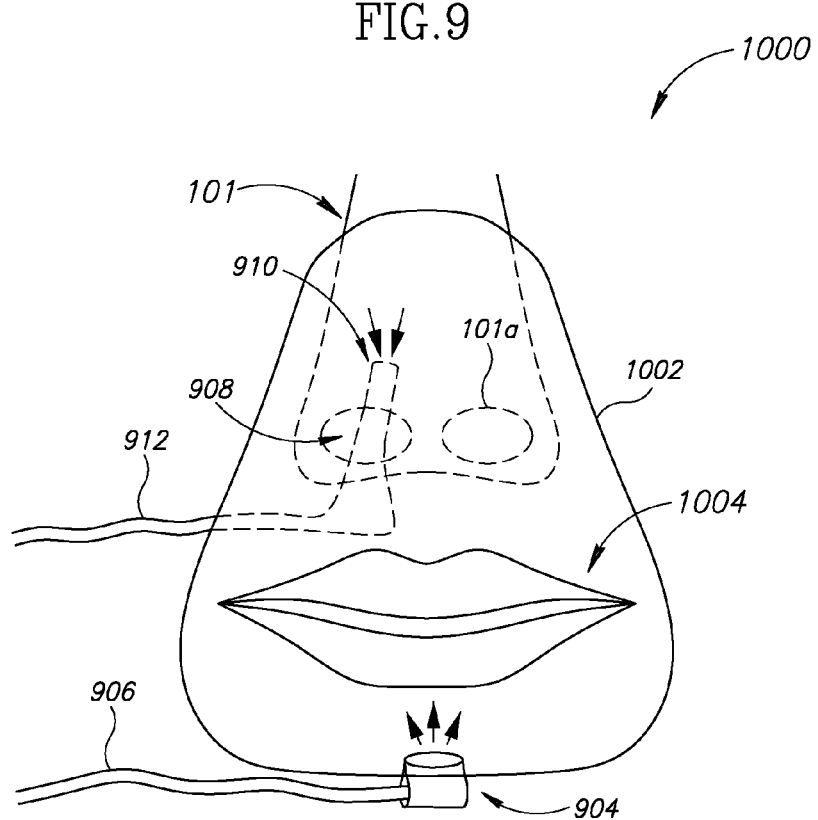

Reference is now made to FIG. 10, which shows a system 1000 similar to system 900 of FIG. 9, but having an oral-nasal mask 1002 covering both the nose and the mouth instead of only the nose, thereby allowing gas to be supplied to both orifices. Similarly, the enlarged distance between gas inlet 904 and distal end 910 may reduce dilution of exhaled breath by supplied gas, thereby improving the reliability of the measurement.

Figure 11A:
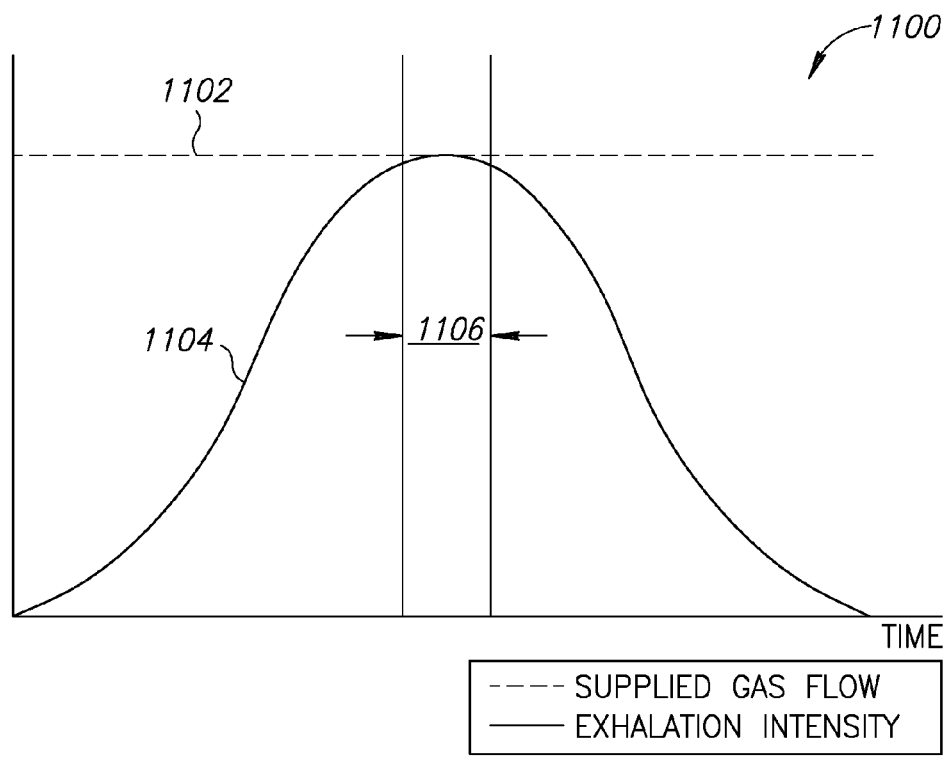
FIGS. 11A-11B show graphs of methods for sampling exhaled breath while gas is being supplied.

Reference is now made to FIG. 11A, which shows a graph 1100 illustrating a method for sampling exhaled breath while gas is being supplied. In this method, sampling of exhaled breath is performed only when the exhalation is at its peak, since at that point, positive pressure created by the exhalation may overcome, at least partially, positive pressure created by the gas supply, so that little or no supply gas enters an exhaled breath sampling cannula. Synchronization of the sampling with the peak of the exhaled breath may be aided by a flow sensor functionally connected to a controller receiving indication of exhalation intensity and timing from the flow sensor and activating the sampling accordingly.

In graph 1100, a gas supply curve 1102 shows a steady rate of gas flow supply, and an exhalation intensity curve 1104 shows a typical, exemplary curve of the intensity of exhalation throughout the entire exhalation. Sampling, in this case, may be performed during a time window 1106, where exhalation is at its peak.

Figure 11B:
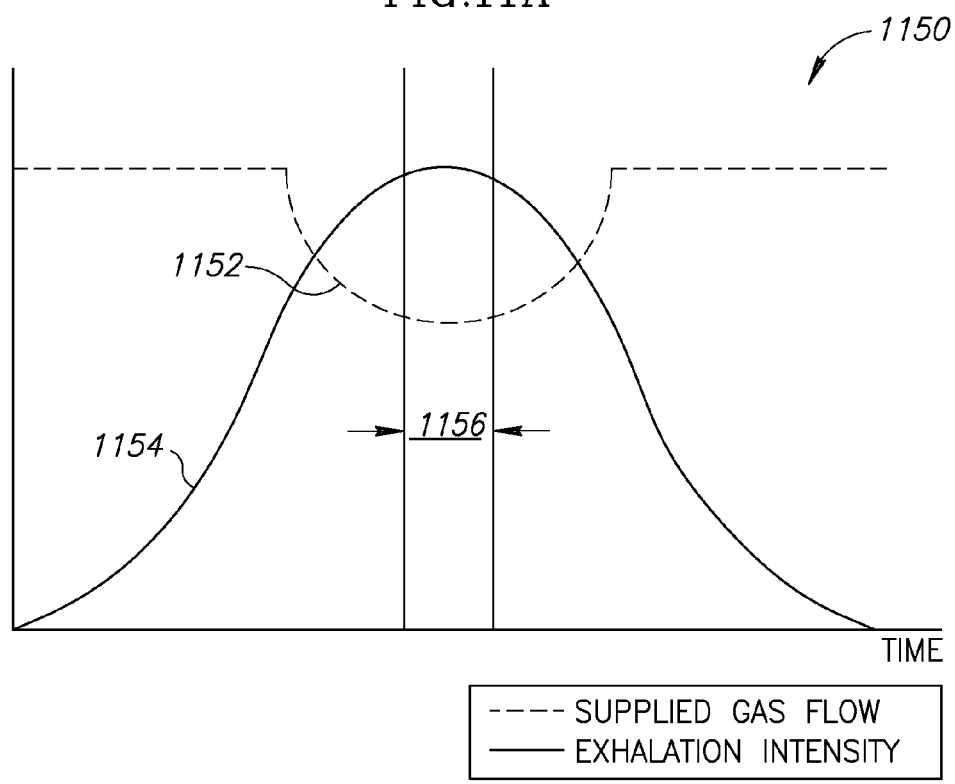

Reference is now made to FIG. 11B, which shows a graph 1150 illustrating an optional variation of the method of FIG. 11A. In graph 1150, the gas supply is reduced throughout approximately the peak of the exhalation intensity 1154, as shown in a gas supply curve 1152. Then, when the exhaled breath is sampled during a time window 1156, less gas flow exists that can dilute the exhaled breath.

Figure 12A:
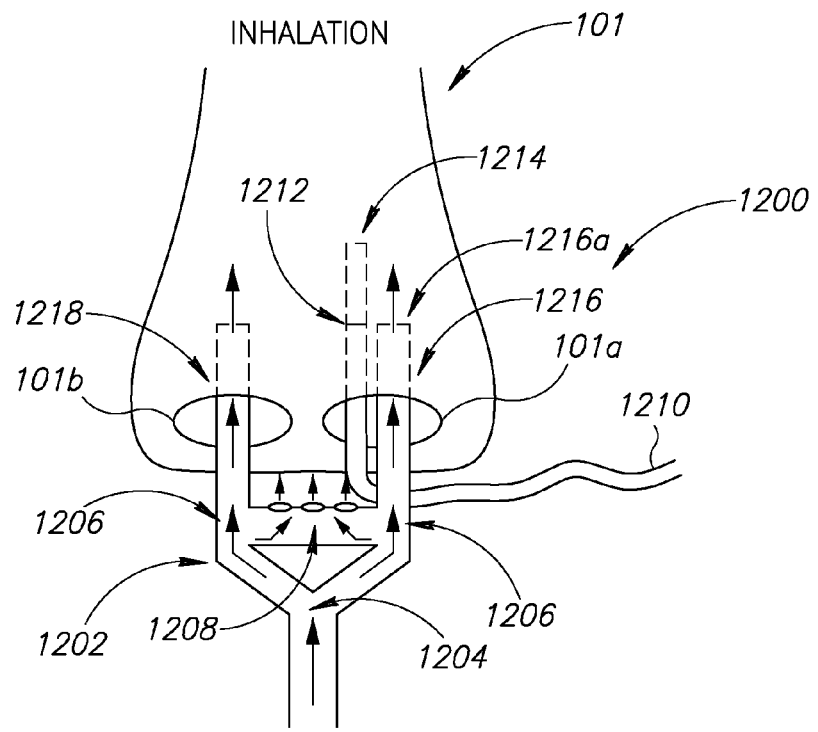
FIGS. 12A-12B show a system adapted for sampling exhaled breath and for supply of a gas.
Figure 12B:
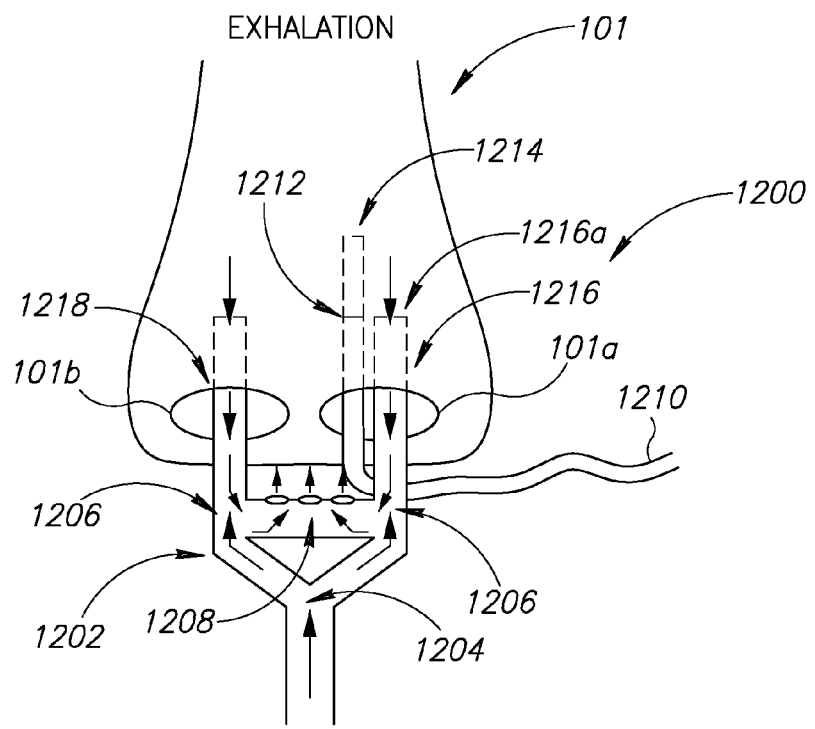

Reference is now made to FIGS. 12A and 12B, which show a system 1200 adapted for sampling exhaled breath and for supply of a gas. System 1200 may include at least one exhaled breath sampling cannula 1210 adapted for insertion into at least one nostril 101a, respectively.

Further, system 1200 may include an aerodynamic gas regulator 1202 adapted to automatically change a flow of gas supply upon inhalation and exhalation. Regulator 1202 may include at least one nasal prong, such as two prongs 1216 and 1218. Regulator 1202 may further include a gas diffuser 1208 including, for example, a plurality of apertures adapted to disperse gas to an area below the nose.

Advantageously, regulator 1202 is configured such that it may supply gas through both of diffuser 1208 and nasal prongs 1216 and 1218 during inhalation, and to supply gas primarily through the diffuser during exhalation, so that dilution of sampled exhaled breath by supplied gas is reduced during exhalation and at yet the gas supply is done nasally during inhalation.

Regulator 1202 may include a Y junction 1204 splitting incoming gas supply into two channels. Each of these channels continues up until nasal prongs 1216 and 1218. The two channels may be connected, at junctions 1206, by a third channel in which diffuser 1208 is disposed.

During inhalation, which is depicted in FIG. 12A, gas flows from the bottom of regulator 1202, splits at Y junction 1204, and splits again at junctions 1206, so that a portion of the gas continues to nasal prongs 1216 and 1218, and a portion of the gas continues to diffuser 1208.

During exhalation, which is depicted in FIG. 12B, gas flows from the bottom of regulator 1202, splits at Y junction 1204, and reaches junctions 1206. At junctions 1206, the gas flow comes against an opposite pressure of the exhaled breath which penetrated through nasal prongs 1216 and 1218. This opposite pressure causes a primary portion of the gas flow to be directed towards diffused 1208 and not up towards nasal prongs 1216 and 1218. Therefore, exhaled breath that is sampled through exhaled breath sampling cannula 1210 during exhalation, may be substantially free of supplied gas.

Exhaled breath sampling cannula 1210 may be inserted into nostril 101a such that its distal end may be either at the same level (shown at 1212) of a distal end 1216a of nasal prong 1216, or deeper (shown at 1214). However, inserting breath sampling cannula 1210 deeper than distal end 1216a may not be necessary, since the aerodynamic nature of regulator 1202 may already mitigate the dilution problem sufficiently.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

What is claimed is:

1. A system for sampling exhaled breath and for supply of a gas, the system comprising:
   a gas delivery cannula comprising at least one nasal prong for insertion into a nostril, said nasal prong comprising a distal end;
   an exhaled breath sampling cannula for insertion into said nostril, said exhaled breath sampling cannula comprising a distal end; and
   a connector for coupling said gas delivery cannula to said exhaled breath sampling cannula, such that the distal end of said exhaled breath sampling cannula is disposed deeper in said nostril than the distal end of said nasal prong, to reduce dilution of sampled exhaled breath by delivered gas,
   wherein said connector is configured to facilitate adjustability of an insertion depth of said exhaled breath sampling cannula into said nostril.

2. The system according to claim 1, wherein said exhaled breath sampling cannula further comprises multiple scale marks indicating gas flow rates, so that said adjustability of the insertion depth can be correlated with a flow rate of delivered gas.

3. The system according to claim 1, wherein said exhaled breath sampling cannula further comprises multiple apertures adjacent to the distal end of said exhaled breath sampling cannula.

4. The system according to claim 1, wherein said nasal prong of said gas delivery cannula further comprises multiple apertures adjacent to the distal end of said nasal prong.

5. The system according to claim 1, further comprising a capnograph connected to a proximal end of said exhaled breath sampling cannula, for measuring a carbon dioxide ($CO_2$) level in exhaled breath.

6. The system according to claim 1, further comprising a gas flow generator connected to said gas delivery cannula, for delivering gas through said gas delivery cannula.

7. The system according to claim 1, wherein said gas comprises oxygen.

8. The system according to claim 1, wherein said exhaled breath sampling cannula is adapted to sample the exhaled breath for measuring a $CO_2$ level.

9. The system of claim 1, further comprising:
   a flow sensor configured to identify a timing and an intensity of an exhaled breath; and
   a controller configured to synchronize sampling of exhaled breath with said timing and intensity, such that exhaled breath is sampled when at a peak of said intensity.

10. The system according to claim 9, wherein said controller is further configured to reduce gas delivery at essentially said peak of intensity.

11. The system of claim 1, further comprising:
   a gas regulator comprising a diffuser, said regulator configured to supply gas through both said diffuser and said nasal prong during inhalation, and to supply gas primarily through said diffuser during exhalation, so that dilution of sampled exhaled breath by supplied gas is reduced during exhalation.

* * * * *